United States Patent
Tokish et al.

[11] Patent Number: 5,683,396
[45] Date of Patent: Nov. 4, 1997

[54] ORTHOPAEDIC CUTTING INSTRUMENTATION WITH CAM LOCKING ARRANGEMENT

[75] Inventors: Leonard J. Tokish, Cordova; Raymond H. Roberson; Abraham B. Salehi, both of Bartlett; Brian Schumacher, Cordova; Gregory C. Marik, Germantown; Jennifer J. Lackey, Memphis, all of Tenn.

[73] Assignee: Smith & Nephew, Inc., Memphis, Tenn.

[21] Appl. No.: 603,630

[22] Filed: Feb. 20, 1996

[51] Int. Cl.[6] .................................................. A61B 17/15
[52] U.S. Cl. ........................... 606/87; 606/82; 606/88; 606/96; 606/79
[58] Field of Search ........................... 606/82, 86, 87, 606/88, 89, 96, 79

[56] References Cited

U.S. PATENT DOCUMENTS

| | | | |
|---|---|---|---|
| 5,395,374 | 3/1995 | Miller et al. | 606/103 |
| 5,484,446 | 1/1996 | Burke et al. | 606/87 |
| 5,514,140 | 5/1996 | Lackey | 606/88 |

Primary Examiner—Michael Buiz
Assistant Examiner—Daphna Shai
Attorney, Agent, or Firm—Pravel, Hewitt, Kimball & Krieger

[57] ABSTRACT

A knee cutting instrument apparatus includes an elongated alignment rod that can enable a surgeon to define alignment with a patient's long bone. An instrument block body can slide upon the alignment rod between its end portions. A locking member forms a connection with the rod at a selected position along the rod. The locking member includes a cam locking arrangement that rotates about a pivot on the instrument body. The cam has a handle portion or arm that enables a user to rotate the cam and its locking tab about its pivot. Part of the locking cam includes a locking tab having a slot that extends circumferentially about ninety degrees (90°) around the pivot of the cam. The slot is positioned radially in between the pivot and the periphery of the locking member at a locking member bearing surface. The slot provides a closed end portion and an open end portion that communicates with the locking member periphery at a positioned spaced away from the bearing surface. The slot is preferably sufficient long enough that it extends circumferentially the full length of the bearing surface.

26 Claims, 3 Drawing Sheets

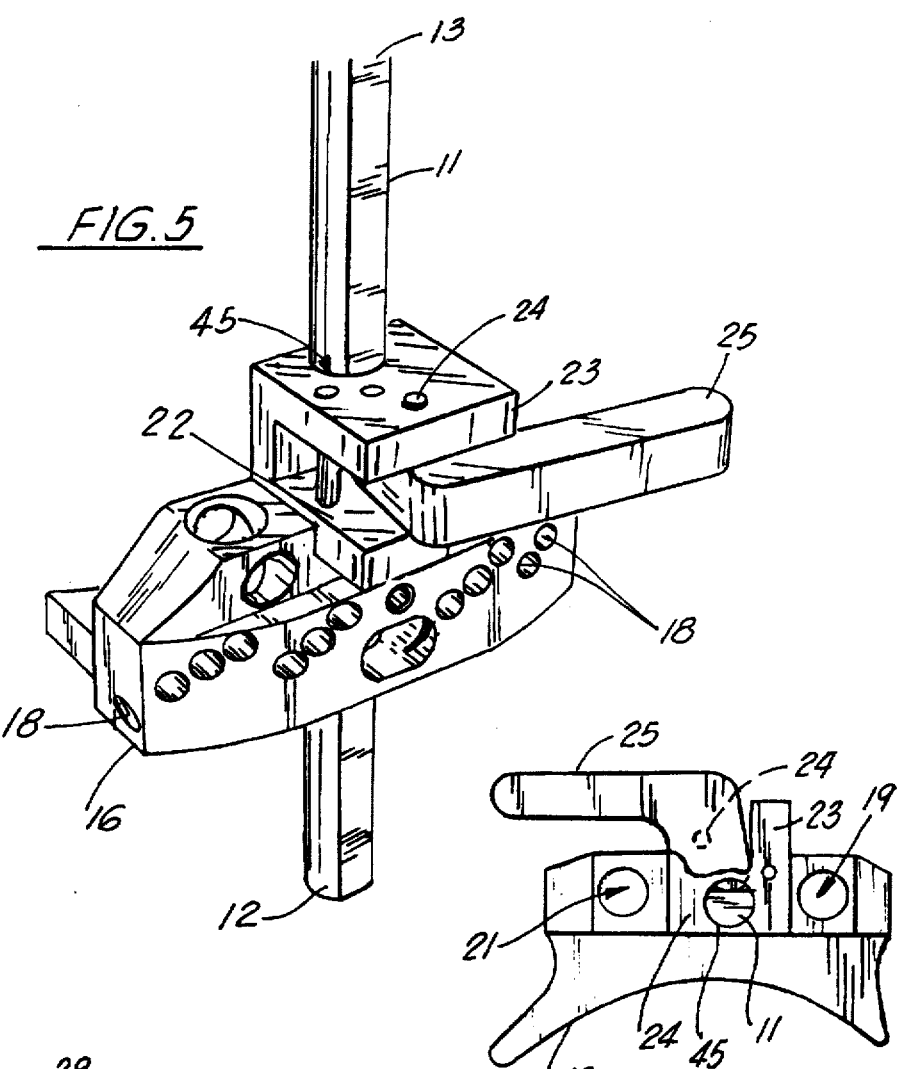
FIG. 5
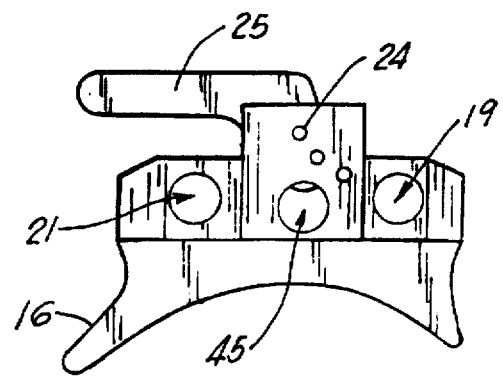
FIG. 6
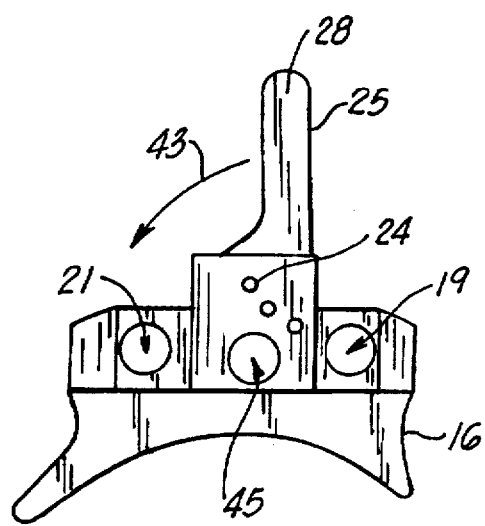
FIG. 7
FIG. 8

ORTHOPAEDIC CUTTING INSTRUMENTATION WITH CAM LOCKING ARRANGEMENT

BACKGROUND OF THE INVENTION

1. Field of the Invention

The present invention relates to medical orthopaedic instrumentation and more particularly relates to an improved bone cutting instrument that includes an elongated alignment rod upon which slides a block body having cutting guide surfaces thereon and wherein a cam locking mechanism cooperates with a longitudinally extending surface of the rod, the cam locking mechanism having an improved configuration that includes an "S" shaped slot that extends at least ninety degrees (90°) circumferentially around the pivot of the cam member.

2. General Background

Many orthopaedic surgical instruments require that use of an elongated rod, plate or bar for alignment purposes. During surgery, this rod can be supported in parallel relationship with a patient's long bone such as for example a patient's tibia or femur. Cutting instruments are often adjustably mounted upon such an alignment rod. It is common to attach tibial or femoral cutting blocks in a sliding manner upon an alignment rod.

One of the most common methods of affixing a tibial cutting block, femoral cutting block or like orthopaedic instrumentation to an alignment rod is a threaded set screw or set bolt that is mounted at the opening in the block through which the rod is mounted. In order to tighten the instrument to a selected position on an alignment rod, the user simply tightens the bolt or set screw so that it engages the outer surface of the rod. In order to move the instrumentation with respect to the rod, the user simply loosens the bolt to disengage it from the rod.

One of the problems of set screw type locking mechanisms is that they tend to loosen very easily. A cam locking mechanism would be desirable in providing a firm locking arrangement between an orthopaedic surgical instrument that is used for cutting patient's bone tissue and an elongated alignment rod. However, one of the problems with cam locking arrangements is that of tolerances. If a cam locking member is manufactured to less than proper tolerances, this affects the locking mechanism and thus the performance of the instrument.

SUMMARY OF THE INVENTION

The present invention provides an improved knee cutting instrument that includes a cutting block body that slides upon an elongated linear alignment rod. A locking member carried by the block body can form a connection with the rod at a selected position along the rod.

The locking member is in the form of a cam that rotates about a pivot pin on the cutting block body. The cam includes an arm portion that enables the user to rotate the cam about its pivot.

The locking member also includes a tab with a bearing surface that engages the rod in a locked position. The user can apply force to the arm when locking the cam bearing surface to the rod. A portion of the locking tab includes a slot that extends circumferentially about the pivot. The slot is also positioned radially in between the pivot pin and the periphery of the locking member in the region of the bearing surface. The slot has a closed end portion and an open end portion. The open end portion communicates with the locking member periphery at a position that is spaced away from the bearing surface.

The slot extends along a curved path circumferentially about the locking member. The slot generally tracks the bearing surface in the region adjacent the bearing surface.

In the preferred embodiment, the slot extends at least ninety degrees (90°) circumferentially about the pivot.

The slot is preferably curved, but a portion of the slot adjacent the bearing surface can be "S" shaped.

The locking member has a center of rotation defined by the pivot pin. The pivot pin extends between two flanges that are an integral portion of the block body.

The slot is preferably very thin (e.g. 0.014 inches thick), being between about 0.006 and 0.10 inches in thickness. The cam 25 is preferably about one to three inches long. In the preferred embodiment, the slot is generally of a uniform thickness along its entire length.

The alignment rod is preferably a cylindrically shaped rod having a portion that is flat. Thus, the rod provides a flat longitudinally extending linear surface thereon for receiving the bearing surface of the locking tab. The alignment rod can be a rectangular or square shaped plate like distal cutting block stylus. However, it should have at least one flat surface.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 5 is a perspective view of the preferred embodiment of the apparatus of the present invention;

FIG. 6 is bottom schematic, partial cut away view of the preferred embodiment of the apparatus of the present invention illustrating the locking cam and its engagement with the alignment rod;

FIG. 7 is a bottom view of the preferred embodiment of the apparatus of the present invention showing the locking cam in a relaxed, unlocked position; and FIG. 8 is a bottom plan view of the preferred embodiment of the apparatus of the present invention illustrating the locking cam in a locked, engaged position.

DETAILED DESCRIPTION OF THE PREFERRED EMBODIMENT

Figure 1:
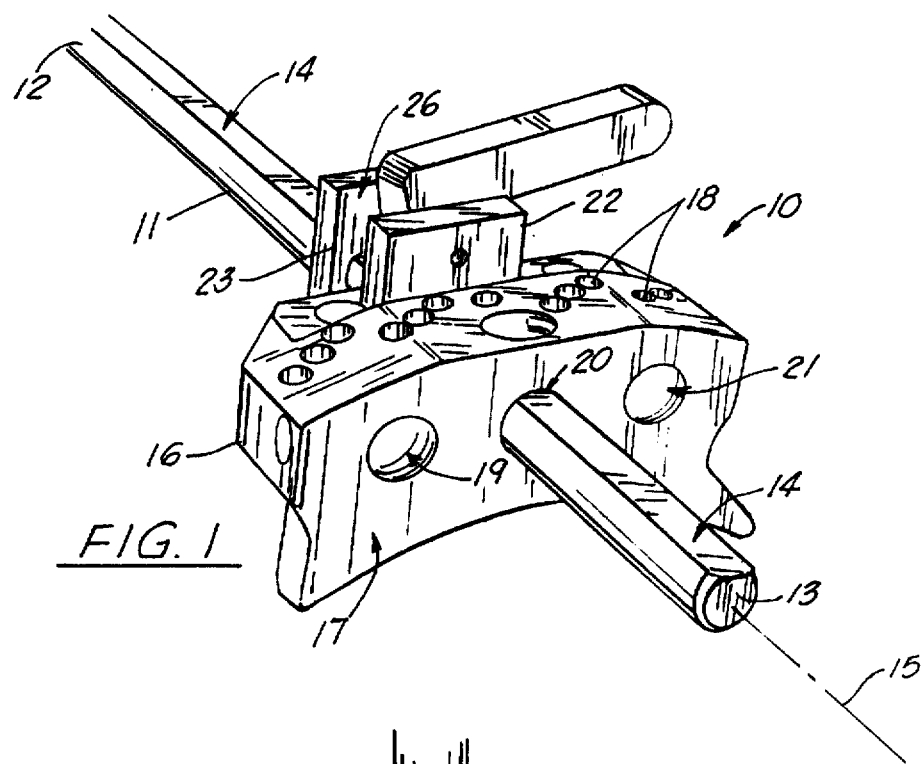
FIG. 1 is a perspective view of the preferred embodiment of the apparatus of the present invention.
Figure 2:
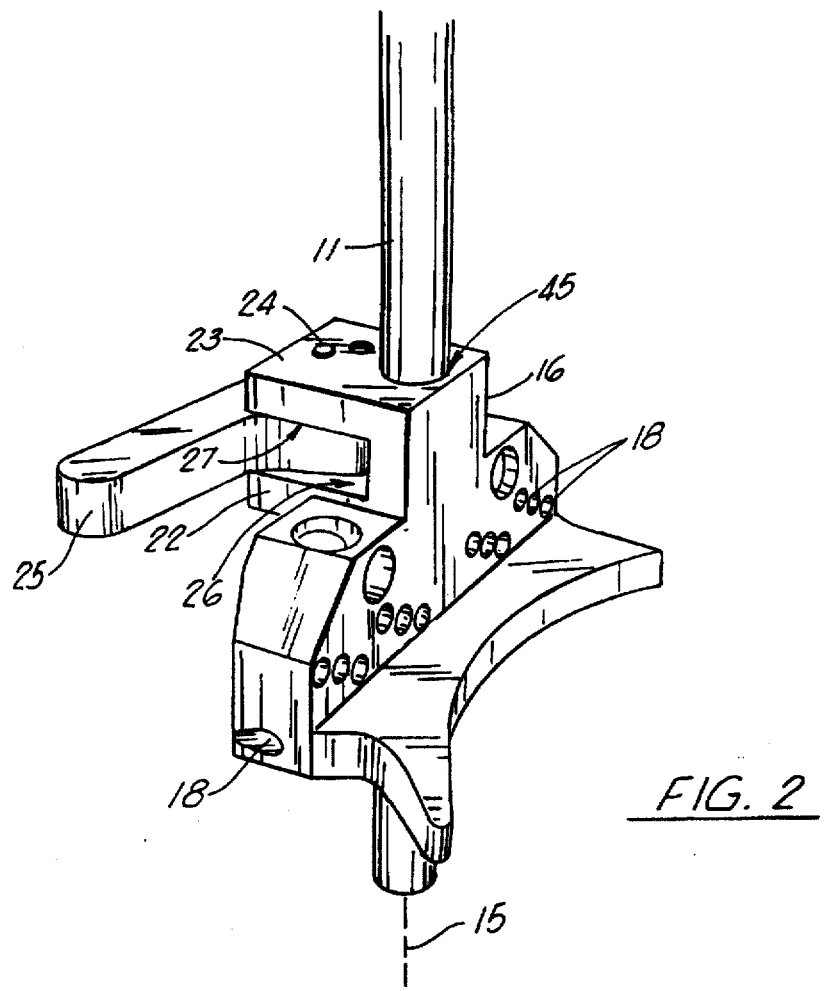
FIG. 2 is another perspective view of the preferred embodiment of the apparatus of the present invention.

FIGS. 1–2 and 5 show generally the preferred embodiment of the apparatus of the present invention designated generally by the numeral 10. Knee cutting instrumentation 10 includes an elongated linear rod 11 having end portions 12, 13, flat longitudinally extending surface 14, and instrument block body 16.

Rod 11 has an elongated rod linear axis 15 that can be aligned by a surgeon with a desired bone that is to be cut as part of a surgical procedure. For example, the rod 11 and its linear axis 15 can be aligned with the central longitudinal axis of a patient's tibia or with a patient's femur. Such a rod 11 can be aligned with the mechanical axis or with the anatomical axis of a patient's bone if desired.

Instrument body 16 can provide one or more cutting guide surfaces 17 thereon. These guide surfaces 17 aid a surgeon by holding a saw blade in a plane while making an appropriate cut on the patient's bone tissue such as for example a patient's proximal tibia, distal femur, or the like.

Instrument block body 16 can also provide a number of openings 18 through which pins or screws can be inserted and then into underlying bone tissue. Such pins or screws are used for rigidifying the block body 16 relative to the patient's bone tissue once alignment is completed using rod 11.

A plurality of bores 19, 20, 21 are provided through body 16 as shown in FIG. 1. The central bore 20 is cylindrically shaped to receive and conform generally to the outer surface of rod 11. A cam locking member 25 is positioned at or near bore 20 for engaging rod 11.

Instrument block body 16 provides a pair of square flanges 22, 23 that are integrally connected thereto as shown in FIGS. 1-2. Each flange 22, 23 has an opening that receives rod 11. Flange 23 has opening 45.

Flanges 22, 23 are spanned by a pivot pin 24 that carries cam locking member 25. The flanges 22, 23 provide flat surfaces 26, 27 that are parallel positioned and accept corresponding flat surfaces 41, 42 of cam locking member 25. During use, the surgeon slides the instrument block body 16 upon rod 11 to a desired location between the ends 12, 13 of rod 11. The surgeon then grabs a handle 28 portion of cam locking member 25 then rotates the handle 28 toward the instrument body 16 in the direction shown by curved arrow 43 in FIG. 7. This causes a bearing surface 30 portion of cam locking mechanism 25 to engage the flat longitudinally extending surface 14 of rod 11 as shown in FIGS. 5-6.

Figure 3:
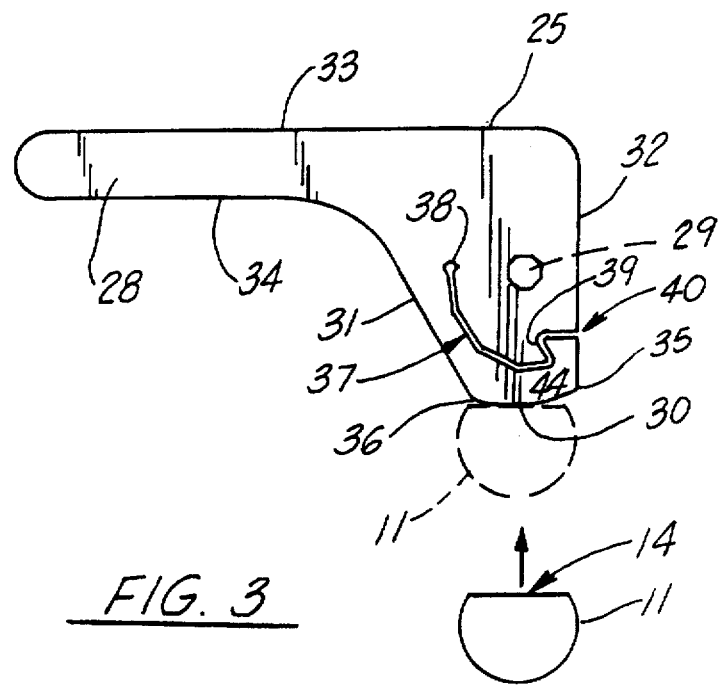
FIG. 3 is a schematic view of the preferred embodiment of the apparatus of the present invention illustrating the cam locking member.
Figure 4:
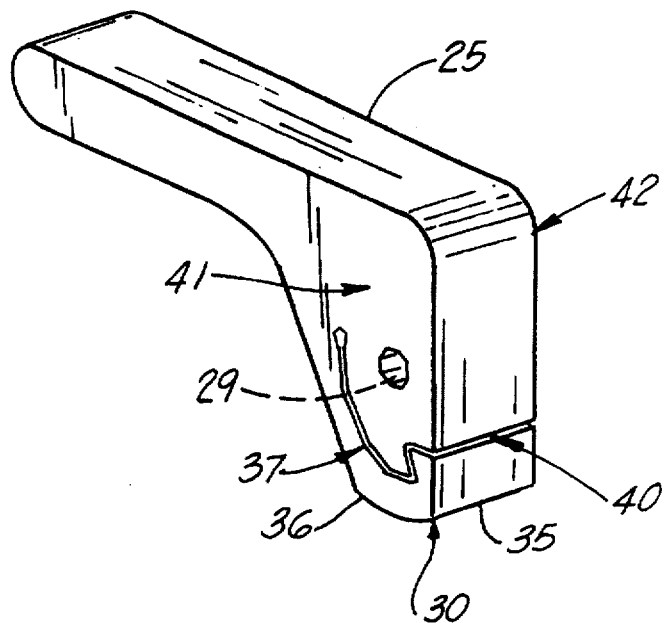
FIG. 4 is another schematic, perspective view of the preferred embodiment of the apparatus of the present invention illustrating the cam locking member.

FIGS. 3-4 show more particularly the construction of the cam locking member 25. Cam locking member 25 has flat parallel surfaces 41, 42 and an elongated slot 37 that extends between surfaces 41 and 42. The slot 37 is preferably of a uniform thickness of between about 0.006 to 0.100 inches. It can be wire cut with a EDM machine. Cam locking member 25 includes a handle 28 portion with a pair of spaced apart flat surface 33, 34. A flat surface 32 is generally perpendicular to the surface 33. Flat surface 31 is angled with respect to surface 34, preferably forming an obtuse angle therewith in FIG. 3. An arcuate surface defines bearing surface 30 as shown in FIG. 3. The bearing surface 30 extends between edges 35, 36. Cam locking member 25 has flat parallel surfaces 41, 42 and an elongated slot 37 that extends between surfaces 41 and 42.

The elongated slot 37 begins at closed end portion 38 and ends at open end portion 40 as shown in FIGS. 3 and 4. An "S" shaped portion 39 is provided closest surface 32. Further, the "S" shaped portion 39 of slot 37 is positioned adjacent to bearing surface 30.

When the surgeon rotates the handle 28 in the direction of arrow 43, the bearing surface 30 also rotates into engagement with the rod 11 and more particularly its flat surface 14. Continued rotate of the handle 28 in the direction of arrow 43 causes the bearing surface 30 to very tightly engage the surface 14 of rod 11. This action produces compression in locking member 25 between pivot pin 24, bearing surface 30 and flat surface 14.

In order to minimize tolerances, the wire cut slot 37 allows a portion 44 of cam locking member 25 to flex. The portion 44 is that portion of cam locking member that is in between the slot 37 and the bearing surface 30, and surfaces 41 and 42 beginning at end 38 and ending at open end 40 of slot 37.

The present invention thus provides a simple yet reliable cam locking arrangement for locking an instrument block body to an elongated alignment rod 11. The present invention solves this problem by providing a unique cam locking arrangement that allows flexibility when the surgeon desires a connection between the cam locking member 25 and the rod 11 at a particular location not withstanding imperfections in manufacture or in assembly.

The following table lists the parts numbers and parts descriptions as used herein and in the drawings attached hereto.

| PARTS LIST | |
|---|---|
| Part Number | Description |
| 10 | knee cutting instrumentation |
| 11 | rod |
| 12 | end |
| 13 | end |
| 14 | flat longitudinal surface |
| 15 | rod linear axis |
| 16 | instrument body |
| 17 | cutting guide surface |
| 18 | opening |
| 19 | bore |
| 20 | bore |
| 21 | bore |
| 22 | flange |
| 23 | flange |
| 24 | pivot pin |
| 25 | cam locking member |
| 26 | flat surface |
| 27 | flat surface |
| 28 | handle |
| 29 | pivot opening |
| 30 | bearing surface |
| 31 | flat surface |
| 32 | flat surface |
| 33 | flat surface |
| 34 | flat surface |
| 35 | edge |
| 36 | edge |
| 37 | wire cut slot |
| 38 | end portion |
| 39 | S shaped portion |
| 40 | open end |
| 41 | flat surface |
| 42 | flat surface |
| 43 | arrow |
| 44 | flex portion |
| 45 | opening |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A knee cutting instrument comprising:
   a) an alignment rod for defining alignment with a patient's long bone;
   b) a cutting instrument that slides upon the alignment rod;
   c) a locking member that forms a connection with the rod at a selected position along the rod, the locking member including a cam member that rotates about a pivot on the cutting instrument, said cam member having a body with an arm for enabling a user to move the cam;

d) the locking member including a portion with a bearing surface that engages the rod, said portion having a slot that extends about the pivot in between the pivot and the periphery of the locking member; and e) the slot having a closed end portion and an open end portion that communicates with the locking member periphery.

2. The knee cutting instrument of claim 1 wherein the slot extends at least ninety degrees about the pivot.

3. The knee cutting instrument of claim 1 wherein the slot has a curved portion.

4. The knee cutting instrument of claim 1 wherein the locking member has opposed flat surfaces and the slot communicates with each of the opposed flat surfaces.

5. The knee cutting instrument of claim 1 wherein the locking member has a center of rotation defined by the pivot, and the arm extends farther from the pivot point than the bearing surface.

6. The knee cutting instrument of claim 1 wherein the slot is between about 0.006 and 0.100 inches in thickness.

7. The knee cutting instrument of claim 1 wherein the slot has an "S"-shaped portion.

8. The knee cutting instrument of claim 1 wherein the slot is about 0.014 inches in thickness.

9. The knee cutting instrument of claim 1 wherein the rod has a flat, longitudinally extending surface thereon.

10. The knee cutting instrument of claim 1 wherein the open end of the slot is spaced away from the bearing surface.

11. A knee cutting instrument comprising:

a) an alignment rod having rod end portions and a linear axis that can be used by a surgeon to define alignment with a patient's long bone;

b) a knee cutting instrument guide that slides upon the alignment rod between the rod end portions;

c) said guide including a locking member that forms a connection with the rod at a selected position along the rod, the locking member including a cam member that rotates about a pivot on the cutting instrument, said cam member having a body with an arm for enabling a user to move the cam member and a locking portion with a bearing surface that engages the rod, said locking portion of the locking member having a curved slot that extends about the pivot in between the pivot and the periphery of the locking member; and d) the curved slot having a closed end portion and a variable radius of curvature.

12. The knee cutting instrument of claim 11 wherein locking portion has a bearing surface at the slot.

13. The knee cutting instrument of claim 12 wherein the slot extends continuously along the bearing surface.

14. The knee cutting instrument of claim 12 wherein the locking member has a center of rotation defined by the pivot, and the arm extends along a first radial line a distance that is farther from the pivot than the distance that the bearing surface extends from the pivot.

15. The knee cutting instrument of claim 12 wherein the rod has a flat, longitudinally extending rod surface thereon, and the bearing surface engages the rod at the flat rod surface.

16. The knee cutting instrument of claim 11 wherein the locking member has opposed flat surfaces and the slot communicates with each of the flat opposed surfaces.

17. The knee cutting instrument of claim 11 wherein the slot is between about 0.006 and 0.100 inches in thickness.

18. The knee cutting instrument of claim 11 wherein the slot has an "S"-shaped portion.

19. The knee cutting instrument of claim 11 wherein the slot is about 0.014 inches in thickness.

20. The knee cutting instrument of claim 11 wherein the open end of the slot is spaced away from the bearing surface.

21. An orthopaedic instrument comprising:

a) a pair of orthopaedic instruments, a first of said instruments having a locking member;

b) wherein the first instrument is movable along a second of the instruments into different positions;

c) wherein the locking member secures the pair of instruments together in a selected position of one instrument relative to the other instrument;

d) the locking member including a cam member that rotates about a pivot on the first instrument, said cam member having a body with an arm that enables a user to rotate the cam between engaged and disengaged positions;

e) the locking member having a locking portion with a periphery that includes a bearing surface that engages the second instrument;

f) a slot that extends generally about the pivot and generally in between the pivot and periphery of the locking member;

g) said slot having a closed end portion; and h) wherein when the locking member is engaged, the bearing surface is in contact with the second instrument.

22. The orthopaedic instrument of claim 21 wherein the slot has an open end portion.

23. The orthopaedic instrument of claim 22 wherein the slot open end portion is spaced away from the bearing surface.

24. The orthopaedic instrument of claim 21 wherein the locking member orients in the same predetermined position when in the engaged position.

25. An orthopaedic instrument comprising:

a) a pair of orthopaedic instruments, a first of said instruments having a locking member;

b) wherein the first instrument is movable along a second of the instruments into different positions;

c) wherein the locking member secures the pair of instruments together in a selected position of one instrument relative to the other instrument;

d) the locking member including a cam member that rotates about a pivot on the first instrument, said cam member having a body with an arm that enables a user to rotate the cam between engaged and disengaged positions;

e) the locking member having a locking portion with a periphery that includes a bearing surface that engages the second instrument;

f) a slot that extends generally about the pivot and generally in between the pivot and periphery of the locking member;

g) said slot having a closed end portion;

h) wherein when the locking member is engaged, the bearing surface is in contact with the second instrument; and i) wherein the locking member includes means for enabling the locking member to surpass a critical peak force at a selected point of travel along its range of motion in between disengaged and the engaged positions, and once the selected point of travel is reached, an applied force prevents further travel of the locking member.

26. An orthopaedic instrument comprising:
a) a pair of orthopaedic instruments, a first of said instruments having a locking member;
b) wherein the first instrument is movable along a second of the instruments into different positions;
c) wherein the locking member secures the pair of instruments together in a selected position of one instrument relative to the other instrument;
d) the locking member including a cam member that rotates about a pivot on the first instrument, said cam member having a body with an arm that enables a user to rotate the cam between engaged and disengaged positions;
e) the locking member having a locking portion with a periphery that includes a bearing surface that engages the second instrument;
f) a slot that extends generally about the pivot and generally in between the pivot and periphery of the locking member;
g) said slot having a closed end portion;
h) wherein when the locking member is engaged, the bearing surface is in contact with the second instrument; and
i) wherein said slot allows deflection of a portion of the locking member upon actuation of the locking member to the engaged position until a peak deflection is surpassed, and wherein any additional deflection applies to a force preventing further cam motion beyond the engaged position.

* * * * *